United States Patent [19]

Basch et al.

[11] Patent Number: 5,553,507
[45] Date of Patent: Sep. 10, 1996

[54] AIRBORNE PARTICULATE

[75] Inventors: Lauren R. Basch, East Greenbush; Harvey Patashnick, Voorheesville, both of N.Y.

[73] Assignee: Rupprecht & Patashnick Company, Inc., Albany, N.Y.

[21] Appl. No.: 461,130

[22] Filed: Jun. 5, 1995

Related U.S. Application Data

[63] Continuation of Ser. No. 370,554, Jan. 9, 1995, abandoned, which is a continuation of Ser. No. 74,930, Jun. 10, 1993, abandoned.

[51] Int. Cl.⁶ .................................................. G01N 1/24
[52] U.S. Cl. .................... 73/863.01; 73/863.11; 73/863.25; 73/863.33
[58] Field of Search ................... 73/28.01, 28.04, 73/863.01, 863.11, 863.21, 863.23, 863.25, 863.33, 863.31, 864.34; 55/270

[56] References Cited

U.S. PATENT DOCUMENTS

| | | | |
|---|---|---|---|
| 3,736,792 | 6/1973 | Poulsen | 73/863.33 |
| 3,765,247 | 10/1973 | Riggs | 73/863.33 |
| 3,784,902 | 1/1974 | Huber | 73/863.23 |
| 3,881,359 | 5/1975 | Culbertson | 73/28.04 |
| 3,999,066 | 12/1976 | Osborn et al. | |
| 4,184,360 | 1/1980 | Vadnay et al. | 73/28.04 |
| 4,382,808 | 5/1983 | Van Wormer, Jr. et al. | 73/863.23 |
| 4,389,903 | 6/1983 | Bertone et al. | 73/863.03 |
| 4,584,887 | 4/1986 | Galen | 73/863.31 |
| 4,649,760 | 3/1987 | Wedding | 73/863.23 |
| 4,696,181 | 9/1987 | Rupprecht et al. | 73/580 |
| 4,813,984 | 3/1989 | Griffis | 73/864.34 |
| 4,838,371 | 6/1989 | Rupprecht et al. | 177/210 FP |
| 5,110,747 | 5/1992 | Patashnick et al. | 422/83 |
| 5,196,170 | 3/1993 | Patashnick et al. | 422/83 |

OTHER PUBLICATIONS

PM–10 Dichotomous Sampler product literature, Graseby Andersen, (Jan., 1992).
PM–10 Medium Flow Sampler product literature, Graseby Andersen, (Jan., 1992).
Ambient Continuous Particulate Monitor product literature, Graseby Andersen, (Jan., 1992).
PM–10 and TSP Hi–vol Samplers product literature, Graseby Andersen, (Jan., 1992).
Sample Inlets TEOM® Series 1200/1400A Ambient Particulate Monitor product literature, Rupprecht & Patashnick Co., Inc. (Jan., 1992).
Continuous PM–10 Monitoring (Most Advanced Technology) product literature, Rupprecht & Patashnick Co., Inc. (Jan., 1992).
TEOM® Series 1400 Ambient Particulate Monitor product literature, Rupprecht & Patashnick Co., Inc. (Jan., 1992).

*Primary Examiner*—Robert Raevis
*Attorney, Agent, or Firm*—Heslin & Rothenberg, P.C.

[57] ABSTRACT

An airborne particulate sampling monitor for collecting particulate in either a solid, liquid or gaseous state. The monitor includes at least two intakes, each of which accepts airborne particulate. Paired with and coupled to each intake is an appropriate particulate filter for sampling accepted airborne particulates. A vacuum pump establishes air flow into one of the intakes and a sampling process controller, coupled between each intake and filter pairing and to the vacuum pump, controls the vacuum pump's establishing of air flow into a selected particulate intake. Preferably, the vacuum pump and sampling process controller reside within a hub unit to which multiple satellite units can be coupled such that each satellite unit employs the vacuum pump and sampling process controller of the hub unit. Due to central processing, conditional sampling at one or more of the units is possible. Further details and manual particulate sampling methods are presented.

37 Claims, 3 Drawing Sheets

AIRBORNE PARTICULATE

This application is a continuation of Ser. No. 08/370,554, filed on Jan. 9, 1995, now abandoned, which was a continuation of Ser. No. 08/074,930, filed Jun. 10, 1993, now abandoned.

TECHNICAL FIELD

The present invention relates generally to sampling of particulates, and more particularly, to a versatile sampler for filtering airborne particulates (in either a solid, liquid or gas state) for subsequent manual removal and quantification/qualification of suspended particulate matter for regulatory and/or scientific utilization.

BACKGROUND ART

Current United States Environmental Protection Agency (EPA) regulations for reference samplers designate the use of a "manual sampling" technique for the measurement of ambient solid particulate concentrations. "Manual sampling" essentially means that a filter is employed in a field unit to continuously sample airborne solid particulates therethrough over a defined period of time. The filter is then manually removed from the field unit and returned to a laboratory for exact measurement of particulate mass collected by the filter.

There are presently two major types of samplers which meet EPA approval as certified particulate reference samplers. These samplers are referred to as "high volume samplers" and "dichotomous samplers." High volume samplers, as the name implies, are systems which utilize a large throughput of air (e.g., 40 CFM) passing through a large filter (e.g., 8 inches×10 inches). The filter is laboratory preweighed and postweighed to determine the mass concentration of particulates within the ambient air over a typical sampling period (e.g., 24 hours). For postweighing, the filter is first reconditioned for, by way of example, a 24 hour period in a controlled temperature and humidity environment. High volume samplers are typically large and not easily transportable by one person. These samplers require the use of a large, high speed blower (pump) to maintain flow and generally require motor maintenance, and even rebuilding, at frequent intervals. If monitoring for more than one 24 hour period is desired, then multiple sampler units must be employed for unattended daily sampling without interruption, such as during a weekend or holiday. There is no standardized temperature history for particulates collected and each one of the multiple samplers is independently operated with no start/stop communication between them. Additionally, there is no provision for conditional sampling capability to allow automatic sampling during specific episodes of interest.

The other major technique employed today, referred to as "dichotomous sampling," operates in a similar fashion to high volume sampling, but utilizes a much lower flow (for example, 16.7 liters/minute), along with smaller filters (e.g., 37 mm in diameter). In a dichotomous sampler, two filters are used to collect particulates downstream from an internal flow divider. The flow stream aerodynamically separates the particulate into coarse (2.5 to 10 microns) and fine (2.5 micron and smaller) size fractions. Both the coarse and fine filters must be conditioned and weighed as noted above, with the sum of the mass on both filters being used along with the volume of air sampled to determine particulate concentration level.

Dichotomous sampling has many of the inherent disadvantages of current high volume sampling. For example, multiple dichotomous samplers must be employed at a monitoring site if extended sampling over a period of days is desired. Further, such samplers depend on flow restricters to maintain constant flow and require manual correction of pressure and temperature to estimate total flow. Large flow errors may occur as accumulated particulate increases the pressure drop across a filter. There is no sampling at standardized temperature and each sampler is independently operated with no stop/start communication between multiple samplers. Dichotomous samplers are not suited for conditional sampling and thereby lack the capability to automatically sample during specific episodes of interest (such as sampling only when the wind is coming from a certain direction or in response to other specific meteorological conditions). In addition, since a dichotomous sampler employs two small filters through which the flow is divided, a sensitive (and expensive) microbalance is required for a laboratory mass weighing accuracy which allows the sum of both filters to provide a particulate mass concentration result. A balance with one microgram sensitivity is typically required, which is a delicate and painstaking instrument to use on a routine basis.

In view of the drawbacks associated with present approaches, a new approach to manual particulate sampling which meets EPA regulations for reference samplers for collecting suspended (solid) particulate matter is needed. The ambient particulate monitor of the present invention provides such a new manual particulate sampler.

DISCLOSURE OF THE INVENTION

As used herein, the terms "particulate" and "particle" encompass minute matter existing in either a solid, liquid or gaseous state. Thus, although principally described with respect to solid matter sampling, the invention is equally applicable to sampling of liquid particles and/or sampling of gasses (such as found in air).

Briefly summarized, the present invention comprises in one aspect a manual sampling monitor for collecting airborne particulate. Multiple air intakes, each of which can accept air flow containing airborne particulate, are associated and paired with multiple particulate filters such that air intake and particulate filter pairings are defined. A vacuum pump establishes air flow into one of the multiple air intakes, with that air intake accepting airborne particulate for collection at its paired particulate filter. A sampling control processor is coupled to each air intake and particulate filter pairing and to the vacuum pump for control of the vacuum pump's establishing of air flow into a selected one of the multiple air intakes. In one embodiment, a primary or hub unit contains a primary air intake and a paired, primary particulate filter, along with the vacuum pump and the sampling control processor. Additional air intakes and their associated particulate filters comprise satellite units which are coupled to the primary unit to take advantage of the vacuum pump and the sampling control processor of the primary unit. Numerous additional enhanced features of the sampling monitor are presented.

In another aspect, the present invention comprises a manual sampling monitor for collecting airborne particulate which includes an intake for accepting air flow containing airborne particulate and a particulate filter coupled thereto for sampling accepted airborne particulate. In this embodiment, the monitor includes a filter holder/exchange mechanism which is manually actuatable between a filter sample position and a filter exchange position. In the filter sample position the particulate filter is sealed within the holder/exchange mechanism for particulate sampling and in the filter exchange position, the holder/exchange mechanism is open for manual removal/replacement of the particulate filter. A vacuum pump establishes air flow into the intake which includes airborne particulate for sampling at the particulate filter.

In yet another aspect, the present invention comprises a manual sampling monitor for collecting airborne particulate which includes an airborne particulate intake for accepting air flow containing particulate and a particulate filter coupled thereto for sampling accepted airborne particulate. A vacuum pump establishes air flow into the intake and a sampling control processor, coupled to the vacuum pump, controls the pump's establishing of air flow into the airborne particulate intake. The sampling control mechanism is structured to receive condition dependent data and employs at least some of this data for conditional activation of the vacuum pump's establishing of air flow into the airborne particulate intake.

In still another aspect, the monitor for manual sampling of airborne particulate is presented. The monitor includes an airborne particulate intake for accepting air flow containing airborne particulate and a particulate filter coupled thereto for sampling accepted airborne particulate. An automated mechanism establishes air flow containing airborne particulate into the airborne particulate intake, and a control mechanism controls the temperature of air flow within the monitor to improve accuracy of any resultant measurement/determination based on sampled particulate.

In but another aspect, the invention comprises a method for sampling airborne particulate employing a manual sampling apparatus. The method includes: establishing an air flow within the manual sampling apparatus; controlling the temperature of the established air flow within the manual sampling apparatus; simultaneous with temperature controlling, sampling particulate at a filter from the established air flow within the manual sampling apparatus; and manually removing the filter from the manual sampling apparatus and evaluating particulate sampled by the filter.

In yet another aspect, the present invention comprises a method for sampling airborne particulate employing a manual sampling apparatus which receives air flow having airborne particulate. The method includes establishing air flow within the manual sampling apparatus; filtering particulate from the air flow within the manual sampling apparatus at a particulate filter; automatically periodically monitoring temperature and pressure of the established air flow within the manual sampling apparatus and determining mass flow therefrom, the mass flow determination employing monitored temperature and pressure of the established air flow to integrate a total mass flow over a sampling period; and manually removing the filter from the manual sampling apparatus and evaluating particulate collected by the particulate filter.

The particulate monitor of the present invention provides many advantages in contrast to the particulate samplers described initially herein. A particulate monitor pursuant to this invention is a portable device which can selectively and intelligently employ a variety of sampling inlets, thereby (for example) allowing collection of particles of a specific size range as desired. A primary unit contains an inlet and filter holder as well as a pump, controller electronics and multiple couplings to satellite units, which may comprise only an inlet and a filter holder. The satellite units are operated through the controller electronics in the primary unit and also utilize the pump and flow controlling system of the primary unit. Thus, additional monitoring capability is readily achieved at minimal cost. All units preferably employ a unique spring loaded, manually actuated filter holder/exchange mechanism for facilitating quick, precise and easy filter exchange even in cold weather.

Both the primary unit and the satellite units have optional heating capability which enables sampling to take place under standardized temperature conditions, and which also allows filter weighing to proceed immediately after collection, thereby eliminating the previous postconditioning step. Flow control can be accurately maintained through the use of a critical flow orifice with temperature and pressure corrections automatically provided by use of a temperature sensor and pressure transducer in combination with appropriate system electronics. A particulate monitor in accordance with the present invention requires only a laboratory balance of 10 micrograms sensitivity, which is considerably less expensive and significantly easier to use than the more sensitive balances required by a dichotomous sampling approach.

BRIEF DESCRIPTION OF THE DRAWINGS

These and other objects, advantages and features of the present invention will be more readily understood from the following detailed description of certain preferred embodiments of the present invention, when considered in conjunction with the accompanying drawings in which.

BEST MODE FOR CARRYING OUT THE INVENTION

Refer now to the drawings wherein the same reference numbers are used throughout multiple figures to designate the same or similar components.

Figure 1:
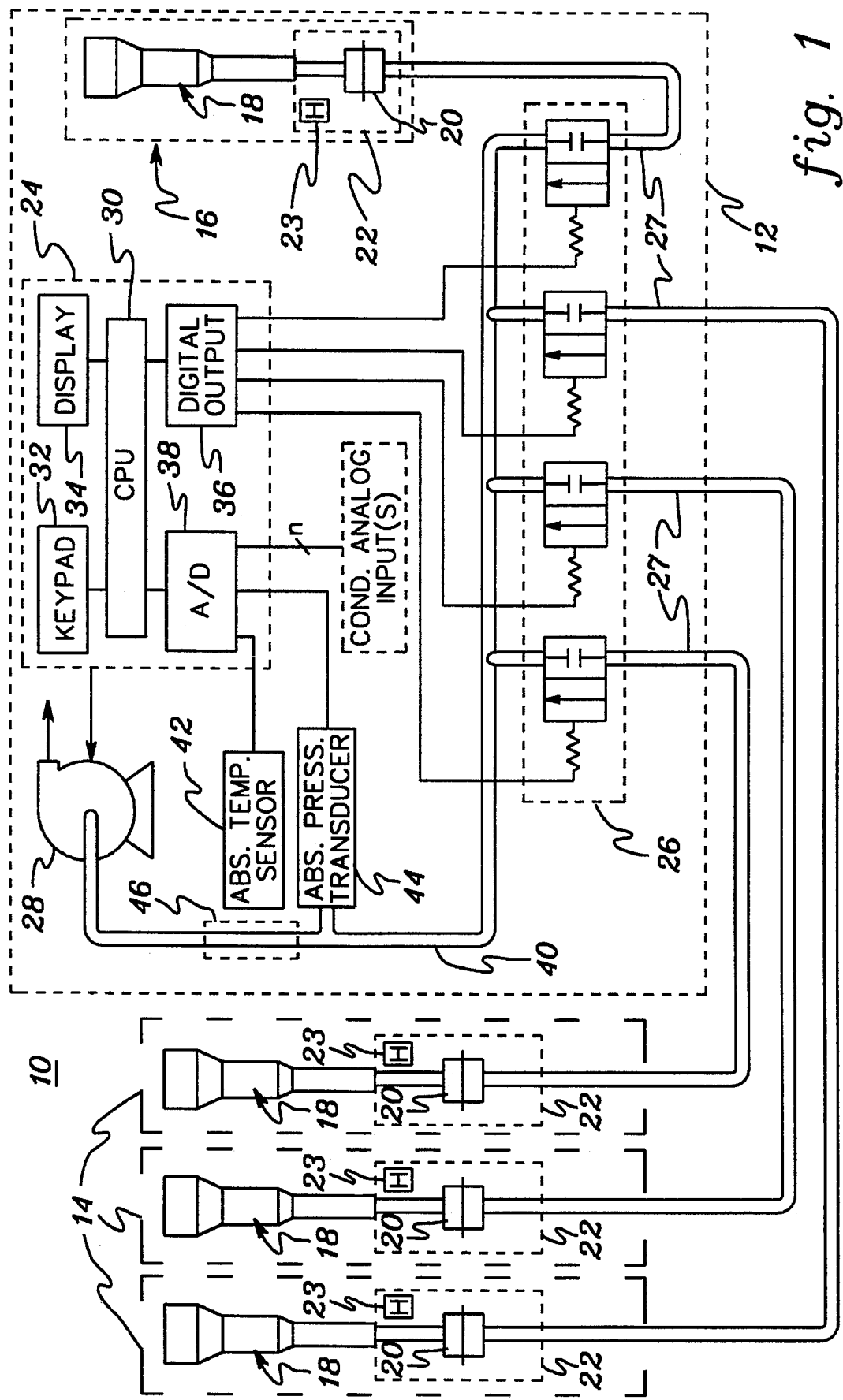
FIG. 1 is a schematic of one embodiment of an airborne particulate sampling monitor pursuant to the present invention.

One electromechanical embodiment of an ambient particulate monitor in accordance with the principles of the present invention is shown in FIG. 1. This particulate monitor, generally denoted 10, includes a primary (or hub) unit 12 and three "slave" or satellite units 14 which are coupled to unit 12. Primary unit 12 includes a primary collection mechanism 16 which has a standard particulate intake 18 paired with a particulate filter 20. Filter 20 resides within a filter holder/exchange mechanism (not shown but discussed below with reference to FIGS. 2–5). The filter holder/exchange mechanism (which may optionally include a heater mechanism 23) is located within a housing 22.

Particulate intake 18 accepts particulate within a predefined range of sizes, for example, ≦10 μm. Such air intake mechanisms are well known in the art and commercially available.

Primary unit 12 further includes a control processor 24, a series of parallel connected solenoids 26 and a vacuum pump 28. As shown, control processor 24 includes a central processing unit (CPU) 30 and appropriate input/output interfaces, such as a keypad 32, a display 34, a digital output buffer 36 and an A/D converter 38. Keypad 32 and display 34 allow an operator to interface with the particulate monitor. Digital output 36 allows process controller 24 to electrically control the parallel coupled solenoids 26 and thereby activation/deactivation of each particulate collection mechanism, whether primary collecting mechanism 16 or a particulate collecting mechanism in one of satellite units 14. Units 14 and primary collecting mechanism 16 are each coupled to a main vacuum tube 40 (which is connected to vacuum pump 28) via one of the parallel coupled solenoids 26 and appropriate vacuum tubing 27. Because a single pump 28 is employed within the monitor, air intake preferably occurs through only one satellite unit or the primary unit at a time.

A/D converter 38 allows process controller 24 to receive n possible conditional analog inputs (wherein n≧1) which, for example, may comprise a monitor signal representative of one or more atmospheric conditions. Preferably, an absolute temperature sensor 42 and an absolute pressure transducer 44 are connected to A/D converter 38 for processor 24 monitoring of air temperature and pressure, respectively, through main vacuum tubing 40. Air flow control is provided by a conventional critical flow orifice 46. Critical flow orifice 46 maintains accurate volume flow control while temperature, pressure and mass flow are determined from the information received by process controller 24 from sensor 42 and transducer 44.

The equation for mass flow through a critical (sonic) orifice is:

$$Q_{mass} = \frac{26.8 \, C_d A P}{\sqrt{T}} \quad (1)$$

Where:

$Q_{mass}$=mass flow (std liter/min)

$C_d$=discharge coefficient (approx. 0.9)

A=orifice throat area (cm^2)

P=upstream absolute pressure (mm Hg)

T=absolute temperature (k)

Therefore, mass flow is directly proportional to the absolute pressure upstream of the critical orifice, and will be affected proportionately by filter loading and barometric changes. For instance, a filter loading of 300 mm Hg will cause the mass flow to decrease by approximately 40 percent from standard conditions.

Volumetric flow is independent of pressure. Since:

$$Q_{vol} = Q_{mass} \cdot \frac{P_{std}}{P} \cdot \frac{T}{T_{std}} \quad (2)$$

Where: $Q_{vol}$=Volumetric flow (lpm)

Solving for $Q_{mass}$ and substituting:

$$Q_{vol} = \frac{26.8 C_d A P_{std} \sqrt{T}}{T_{std}} \quad (3)$$

Thus the volumetric flow is not affected by the pressure at the critical orifice. Volumetric flow is affected inversely by the square root of the absolute temperature. However, over the range of −30° to +40° C. this volumetric change is less than +/−8% and so does not significantly change the performance of the inlet.

In one embodiment, vacuum pump 28 comprises a low volume induction motor vacuum pump which, for example, may be set up to pump 16.7 liters per minute through a selected one of the satellite units or the particulate collecting mechanism of the primary unit. This flow rate is selected to take advantage of existing intake mechanisms, such as those now employed by dichotomous samplers. However, unlike the dichotomous sampler, the present invention employs a single filter to capture all particulate. As a consequence, a balance of less sensitivity can be used to manually measure the resultant mass. For example, a 10 microgram sensitivity balance may be employed.

As noted, connected to primary unit 12 are multiple satellite units 14, with three such units being shown in FIG. 1 by way of example. Each satellite unit is activated/deactivated by processor controller 24 via a corresponding one of the parallel connected solenoids 26. Again, vacuum tubing 27 connects each satellite unit to its respective solenoid mechanism 26. Each satellite unit 14 comprises essentially the same structure as particle collecting mechanism 16 disposed within primary unit 12.

In particular, each satellite unit 14 includes an air intake mechanism 18 which has an associated particulate filter 20, disposed downstream thereof. Each intake mechanism 18 accepts airborne particulate substantially within a predetermined size range (e.g., ≦10 μm) for collection at its associated filter 20. Each filter 20 is disposed within an appropriate housing 22 which is preferably sealed when the unit is sampling and may be heat controlled 'H' 23 from process controller 24 within primary unit 12. (The specific electrical connections to accomplish heat control with an appropriate feedback temperature sensor will be understood by one skilled in the art and are not shown in FIG. 1 for drawing simplicity.)

Figure 2:
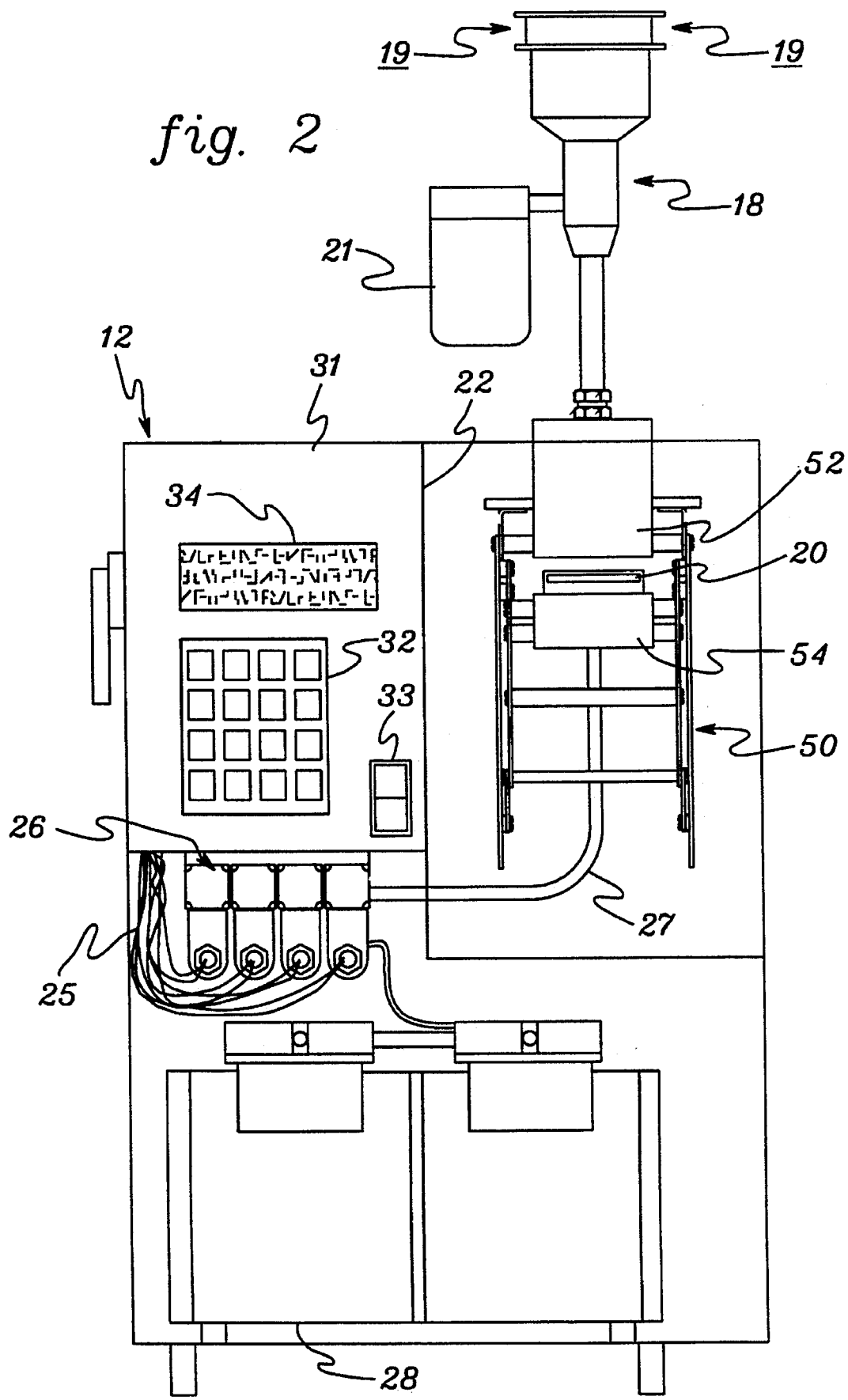
FIG. 2 is a partial elevational view of one structural embodiment of the primary unit of the airborne particulate sampling monitor of FIG. 1.

A mechanical embodiment of primary unit 12 is depicted in FIG. 2. An air stream 19 is established into intake mechanism 18 and particulate within a predetermined size range defined by the intake are passed through to a filter 20. Filter 20 resides within a holder/exchange mechanism 50, one embodiment of which is shown in FIG. 2 in a partially open, nonoperative position. Filter 20 resides within an upper rim funnel structure 52 and a lower rim funnel structure 54 and is sealed therein when closed, for example, by an upper elastomeric seal and a lower elastomeric seal (not shown). Particulate intake 18 may employ a water collector 21, commonly used today in dichotomous and continuous samplers to remove condensed water from an air stream. A housing 22 surrounds the filter and its holder/exchange mechanism 50.

Air flow passing through filter 20 proceeds via vacuum tubing 27 and an appropriate one of the parallel coupled solenoids 26 to vacuum pump 28 disposed in a lower portion of primary unit 10. The solenoids are electrically controlled through lead lines 25 connected to process controller 24 disposed behind a panel 31, which contains keypad 32 and display 34. A monitor on/off switch 33 is also provided. Although not shown, each satellite unit (if needed) could be mechanically similar to intake mechanism 18 and its associated filter 20, and could employ a filter holder/exchange mechanism such as mechanism 50. However, only primary unit 10 contains the vacuum pump 28 and control electronics 24 (FIG. 1).

Figure 3:
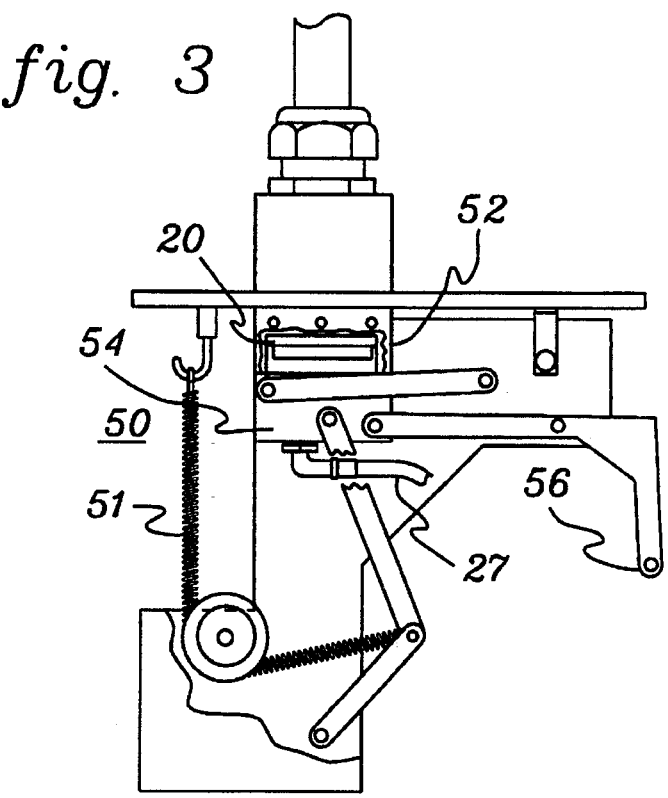
FIG. 3 is a side elevational view of one embodiment of a filter loading mechanism pursuant to the present invention, for use in the sampling monitor of FIGS. 1 & 2, the filter loading mechanism being shown in a closed position.
Figure 4:
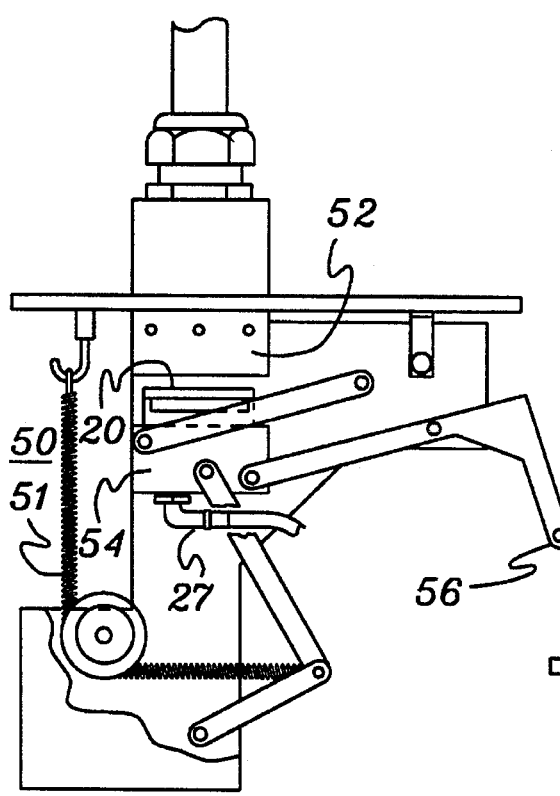
FIG. 4 is a side elevational view of the filter loading mechanism embodiment of FIG. 3, shown in a partially open position.
Figure 5:
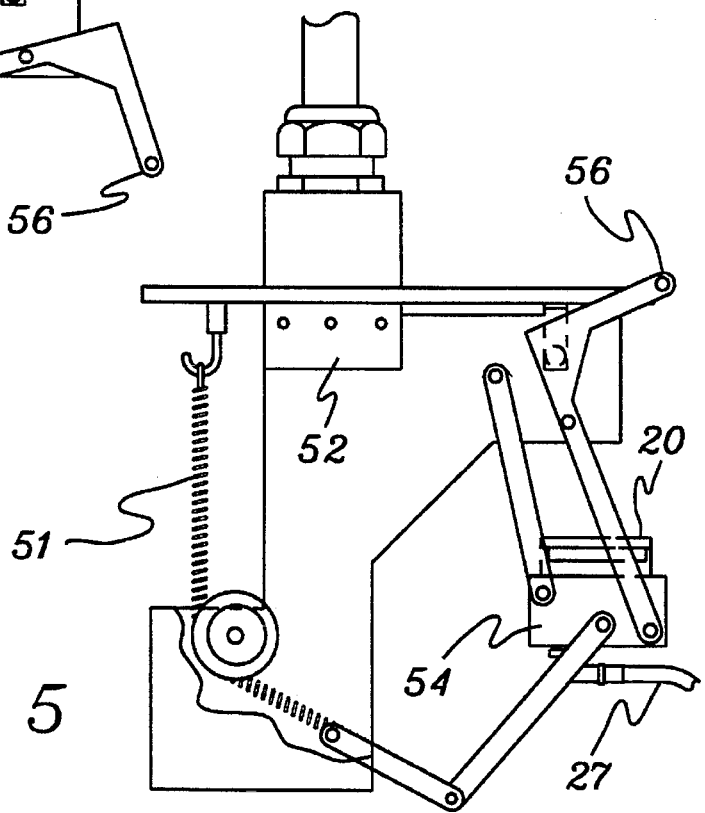
FIG. 5 is a side elevational view of the filter loading mechanism embodiment of FIGS. 3 & 4, shown in a full open position for the manual removal/insertion of a filter.

The structure and operation of filter holder/exchange mechanism 50 can be understood from the side elevational depictions thereof presented in FIGS. 3–5. In FIG. 3, mechanism 50 is shown in a closed position wherein the filter 20 (shown in the cutaway) is in operative position sealed between upper rim 52 and lower rim 54. After passing through the filter, air flow proceeds via vacuum tubing 27 to main tubing 40 and hence vacuum pump 28 (FIG. 2). Mechanism 50 comprises a unique spring (51) loaded, manually actuated apparatus for quick, precise and easy exchanging of a filter, even in inclement weather. To open, a handle 56 is manually actuated outward and upward such that lower rim 54 (again, which holds filter 20) is pivoted downward and outward from mechanism 50. Mechanism 50 is shown partially open in FIG. 4 and fully open in FIG. 5 (for easy manual removal/exchange of filter 20.) Tubing 27 must be flexible and of sufficient length so as not to interfere with the desired pivoting movement of lower rim 54. In a simple swing motion the mechanism may be opened or, conversely, closed. (Again, an appropriately sized elastomeric seal would be located above and below filter 20 to seal the filter within the upper and lower rims of mechanism 50 when closed.)

Each particulate filter may be of a different size, but standardization is believed preferable and a circular 47 millimeter diameter filter is one possibility for the collection of respirable particulate less or equal to 10 microns in size. (As noted initially, the novel concepts described herein are equally applicable to collection of particulate in solid, liquid or gaseous state. If gas particles are to be sampled then any gas sorption media may be employed as the particulate filter.)

From the above discussion, those skilled in the art will recognize that one feature of a sampling monitor in accordance with a certain aspect of the present invention is the ability to selectively add satellite sampling units to the hub unit, with each satellite unit being controlled by and utilizing the pump and electronics of the main (hub) sampling unit. Thus, start and stop times and accurate flow information can be determined for each sampler by the electronics of the hub unit. There are several advantages to this approach. First, once the hub unit is purchased additional sampling capacity is available at significantly lower cost. This means that a monitoring station requiring, for example, three samplers to provide 24 hour sampling over a weekend (when manpower to change filters is generally not available) can be inexpensively obtained in comparison with monitors where multiple, totally independent and complete units must be employed.

Secondly, in accordance with the principles of the present invention conditional sampling can be readily implemented so that the hub unit or any one of the multiple satellite units can be instructed to sample when an input(s) from another monitoring device (such as a wind direction monitor) indicates that sampling is desirable. Third, sampling histories for the hub unit and each satellite unit can be easily stored by the hub electronics (e.g., in random access memory) for post-sampling data analysis. Additionally, since the hub unit utilizes a small, low-volume pump and since the satellite units employ no other pump, the system is readily portable enabling set up at a desired monitoring site with minimal manpower.

The use of a microprocessor electronic controller also permits very accurate flow information to be inexpensively obtained. Since each sampler utilizes, for example, a commercially available inlet to establish a particle cut point for the sample stream, a constant volumetric flow should be maintained to ensure proper performance of the inlet. This is most easily accomplished by employing a critical flow orifice upstream from the pump, which is a standard method of flow control. The problem is that although the technique maintains nearly constant volume flow, determination of particle mass concentration requires knowledge of the sampled volume corrected to standardized pressure and temperature. Some samplers utilize "gross" seasonal corrections in data analysis to address this problem. With the processor electronics of a manual monitor pursuant to the present invention, continuous, repetitive measurement of pressure and temperature is possible so that an exceptionally accurate standardized sample volume can be computed and provided for final data analysis.

Another feature of the present invention which is believed unique in connection with manual sampling is the ability to maintain a constant sample stream temperature and filter temperature. This is practical because of the relatively low flow and filter size as well as the ability of the microprocessor-based electronics to control temperature. The concept is implemented by providing a heater on the inlet mechanism(s) to heat the sample flow path and a heater within the filter cartridge holder block (i.e., housing 22 in FIG. 1). Although an option, the feature may have significance in the future since current United States EPA requirements for particulate monitoring are scientifically ambiguous due to nonspecified collection temperatures. Presently, manual samplers collect at ambient temperatures. Due to volatile components within the particulate, inconsistencies can result, for example if a sampler is positioned in the sun vs. the shade, especially if the filter remains in place after sampling time has elapsed. It is not practical to provide temperature control on current samplers. Should EPA become more scientifically rigorous in this field, therefore, this feature will prove important. Another potential advantage to a heated system is that the filter can be removed, placed in a sealed container, and brought back to a laboratory where it can be weighed immediately, without undergoing the typical long wait associated with today's filter postconditioning.

A mechanical feature of a sampling monitor in accordance with the present invention is the filter exchange mechanism depicted in the drawings. A filter is held between two (e.g., plastic) rims, the lower rim containing a filter screen. This entire assembly is situated in a rectangular filter holder block which is able to move between two positions, one for sampling and the other for filter exchange. A series of parallel linkages which are spring loaded provide the required motion when a handle between the linkage is pushed or pulled appropriately. This exchange mechanism is a substantial improvement compared to current samplers which typically require bolting the filter between flanges or screwing a ring around the filter support rim to provide a seal.

Although specific embodiments of the present invention have been illustrated in the accompanying drawings and described in the foregoing detailed description, it will be understood that the invention is not limited to the particular embodiments described herein, but is capable of numerous rearrangements, modifications and substitutions without departing from the scope of the invention. The following claims are intended to encompass all such modifications.

We claim:

1. A manual sampling monitor for collecting airborne particulate, said manual sampling monitor comprising:

at least two airborne particulate intakes;

at least two particulate filters, each particulate filter being paired with and coupled to a different one of said at least two intakes for collecting airborne particulate;

vacuum pump means for establishing air flow into a selected one of said at least two intakes, said selected one of said at least two intakes accepting particulate in the established air flow for collection at its paired particulate filter;

a single automated sampling control means electromechanically coupled to each intake and particulate filter pairing and to said vacuum pump means for control of said vacuum pump means' establishing of air flow into said selected one of said at least two airborne particulate intakes;

multiple filter holder/exchange mechanisms and associated housings, each filter holder/exchange mechanism having a pivoting mechanism and being actuatable using said pivoting mechanism between a filter sample position and a filter exchange position, and wherein each of said at least two particulate filters is held within its own filter holder/exchange mechanism, and each filter holder/exchange mechanism resides within its own associated housing; and means for controlling temperature within said filter holder/exchange mechanism housings, said temperature control means being coupled to and controlled by said sampling control means.

2. The manual sampling monitor of claim 1, wherein each filter holder/exchange mechanism includes an upper rim block and a lower rim block between which the associated particulate filter is held, and wherein when a filter holder/exchange mechanism is in said filter sample position, its upper rim block and its lower rim block are sealed together about the associated particulate filter such that any airborne particulate accepted by the paired intake means is sampled by said particulate filter, and wherein when said filter holder/exchange mechanism is in said filter exchange position, its upper rim block and its lower rim block are spaced apart for manual insertion/removal of the particulate filter.

3. The manual sampling monitor of claim 1, wherein said sampling control means includes a process controller and multiple solenoid valves, each solenoid valve being coupled between one of said intake and particulate filter pairings and said vacuum pump means, said process controller including means for selectively activating and deactivating said multiple solenoid valves for selective control of said vacuum pump means' establishing of air flow into said selected one of said at least two airborne particulate intakes.

4. The manual sampling monitor of claim 1, further comprising means for controlling volume flow within said sampling monitor, said volume flow within said sampling monitor being based on a rate of air flow into said selected one of said at least two air intakes having said established air flow.

5. The manual sampling monitor of claim 4, further comprising means for monitoring mass flow, said mass flow monitoring means includes a temperature sensor and a pressure transducer disposed so as to monitor temperature and pressure, respectively, of air flow within said manual sampling monitor.

6. The manual sampling monitor of claim 5, wherein said means for controlling the rate of air flow within said manual sampling monitor is separate from said vacuum pump means.

7. The manual sampling monitor of claim 6, wherein said flow control means comprises a critical flow orifice, and wherein said temperature sensor and pressure transducer are disposed in an air flow direction upstream from said critical flow orifice.

8. The manual sampling monitor of claim 1, further comprising means for inputting external condition dependent data to said sampling control means, said sampling control means including means for employing at least some of said external condition dependent data for conditional activation of said selected one of said at least two airborne particulate intakes.

9. The manual sampling monitor of claim 1, wherein said vacuum pump means comprises a low volume, induction motor vacuum pump.

10. The manual sampling monitor of claim 1, wherein each of said at least two intakes accepts airborne particulate sized substantially within a same predetermined range.

11. Manual sampling apparatus for collecting airborne particulate, said manual sampling apparatus comprising:

a primary unit, said primary unit including:
  primary collecting means having an intake and an associated particulate filter for collecting airborne particulate from an air stream into said intake,
  vacuum pump means for establishing said air stream into said intake of said primary collecting means,
  automated sampling control means coupled between said primary collecting means and said vacuum pump means for controlling establishing of said air stream into said intake of said primary collecting means;

at least one satellite unit, each at least one satellite unit having its own satellite collecting means including an intake and a particulate filter for collecting airborne particulate from an air stream into said satellite collecting means;

said at least one satellite unit being coupled to said primary unit such that said vacuum pump means of said primary unit is coupled to each satellite collecting means and such that said automated sampling control means of said primary unit controls activation and deactivation of each satellite collecting means of said at least one satellite unit; and means for inputting external condition dependent data to said sampling control means, said sampling control means including means for employing at least some of said external condition dependent data for conditional activation of one of said primary collecting means of said primary unit and said satellite collecting means of said at least one satellite unit.

12. The manual sampling apparatus of claim 11, wherein said sampling control means includes a process controller and multiple solenoid valves, each solenoid valve being coupled between said vacuum pump means and one of said primary collecting means and said satellite collecting means, said process controller selectively activating and deactivating said multiple solenoid valves for selective control of said vacuum pump means' establishing of said air stream into one of said primary collecting means and said satellite collecting means.

13. The manual sampling apparatus of claim 11, wherein each at least one satellite unit is remotely spaced from said primary unit.

14. The manual sampling apparatus of claim 11, wherein said primary collecting means and said satellite collecting means accept airborne particulate sized substantially within a same predetermined size range.

15. Manual sampling monitor for collecting airborne particulate, said manual sampling monitor comprising:

an airborne particulate intake for accepting air flow containing airborne particulate;

a particulate filter coupled to said airborne particulate intake for sampling accepted airborne particulate;

a filter holder/exchange mechanism having a pivoting mechanism and being actuatable using said pivoting mechanism between a filter sample position and a filter exchange position, said particulate filter being sealed within said filter holder/exchange mechanism when in said filter sample position, and when in said filter exchange position said holder/exchange mechanism being open with said particulate filter vertically and horizontally displaced from said filter sample position to facilitate manual removal/replacement of said particulate filter; and vacuum pump means for establishing air flow into said airborne particulate intake, said air flow containing airborne particulate for sampling by said particulate filter.

16. The manual sampling monitor of claim 15, wherein said filter holder/exchange mechanism resides within a housing and wherein said monitor further comprises means for controlling temperature of said filter holder/exchange mechanism housing.

17. The manual sampling monitor of claim 15, further comprising automated sampling control means coupled to said airborne particulate intake and said vacuum pump means for control of said vacuum pump means' establishing of air flow into said airborne particulate intake.

18. The manual sampling monitor of claim 17, further comprising means for inputting external condition dependent data to said sampling control means, said sampling control means including means for employing at least some of said external condition dependent data for conditional activation of said air flow into said airborne particulate intake.

19. The manual sampling monitor of claim 15, wherein said vacuum pump means comprises a low volume, induction motor vacuum pump.

20. A manual sampling monitor for collecting airborne particulate, said manual sampling monitor comprising:

an airborne particulate intake for accepting air flow containing airborne particulate;

a particulate filter coupled to said airborne particulate intake for sampling accepted airborne particulate;

vacuum pump means for establishing air flow into said intake, said air flow containing airborne particulate for sampling by said particulate filter; and automated sampling control means coupled to said vacuum pump means for control of said vacuum pump means' establishing of air flow into said airborne particulate intake, said sampling control means having means for receiving external condition dependent data and for employing at least some of said external condition dependent data for conditional activation of said vacuum pump means' establishing of air flow into said airborne particulate intake.

21. The manual sampling monitor of claim 20, wherein said sampling control means includes means for monitoring mass flow within the manual sampling monitor, said mass flow monitoring means including means for controlling the rate of air flow within the manual sampling monitor and a temperature sensor and a pressure transducer disposed so as to monitor temperature and pressure, respectively, of the air flow within the manual sampling monitor.

22. The manual sampling monitor of claim 20, wherein said vacuum pump means comprises a low volume, induction motor vacuum pump.

23. A monitor for manual sampling of airborne particulate, said monitor comprising:

an airborne particulate intake for accepting air flow containing airborne particulate;

a particulate filter coupled to said airborne particulate intake for sampling accepted airborne particulate;

means for establishing air flow containing airborne particulate into said airborne particulate intake; and means for raising the temperature of air flow within said monitors, wherein once said particulate filter is manually removed from said manual sampling monitor, particulate collected by said filter can be immediately analyzed.

24. The manual sampling monitor of claim 23, further comprising means for controlling volume flow within said sampling monitor, said volume flow within said sampling monitor being based on a rate of air flow into said airborne particulate intake.

25. The manual sampling monitor of claim 24, further comprising means for controlling mass flow, said mass flow controlling means including a temperature sensor and a pressure transducer disposed so as to monitor temperature and pressure, respectively, of air flow within the manual sampling monitor.

26. A method for sampling airborne particulate employing a manual sampling apparatus which accepts airborne particulate, said method comprising the steps of:

(a) establishing an air flow through said manual sampling apparatus;

(b) raising the temperature of said air flow through said manual sampling apparatus established in said step (a);

(c) simultaneous with said temperature raising step (b), filtering particulate from said air flow through said manual sampling apparatus at a particulate filter;

(d) manually removing said filter from said manual sampling apparatus; and (e) evaluating particulate collected by said particulate filter during said filtering step (c), wherein said raising step (b) facilitates said evaluating step (e) to be immediately performed after said manual removing step.

27. The method of claim 26, wherein said manual sampling apparatus includes multiple particulate filters and wherein said method further comprises the step of selecting between said multiple particulate filters within which to perform said particulate filtering step (c).

28. The method of claim 27, further comprising the step of monitoring at least one condition external to the manual sampling apparatus, and wherein said filter selecting includes selecting between said multiple particulate filters based upon said condition monitoring.

29. A satellite sampling apparatus for use with a primary sampling apparatus for collecting airborne particulate, said primary sampling apparatus having a primary intake, a primary particulate filter and a vacuum pump, said satellite sampling apparatus comprising:

a satellite intake for accepting an air stream;

a satellite particulate filter for collecting the airborne particulate from said air streams;

means for connecting said satellite intake to the vacuum pump of the primary sampling apparatus; and a satellite filter holder/exchange mechanism having a pivoting mechanism and being actuatable using said pivoting mechanism between a filter sample position and a filter exchange position, said satellite particulate filter being sealed within said satellite filter holder/exchange mechanism when in said filter sample position, and when in said filter exchange position said satellite filter holder/exchange mechanism being open with said satellite particulate filter vertically and horizontally displaced from said filter sample position to facilitate manual removal/replacement of said particulate filter.

30. The apparatus of claim 29, wherein said satellite sampling apparatus is remote from said primary sampling apparatus and coupled thereto by vacuum tubing.

31. A satellite sampling apparatus for use with a primary sampling apparatus for collecting airborne particulate, said primary sampling apparatus having a primary intake, a primary particulate filter and a vacuum pump, said satellite sampling apparatus comprising:

a satellite intake for accepting an air stream;

a satellite particulate filter for collecting the airborne particulate from said air stream;

means for connecting said satellite intake to the vacuum pump of the primary sampling apparatus; and a heater for raising the temperature of air flow within said satellite sampling apparatus, wherein once said satellite particulate filter is manually removed from said satellite sampling apparatus, particulate collected by said satellite particulate filter can be immediately analyzed.

32. A manual sampling monitor for collecting airborne particulate, said manual sampling monitor comprising:

multiple airborne particulate intakes for accepting air flow containing airborne particulate;

multiple particulate filters of which each particulate filter is coupled to its own airborne particulate intake of said multiple airborne particulate intakes for sampling accepted airborne particulate;

a filter holder/exchange mechanism having a pivoting mechanism and being actuatable using said pivoting mechanism between a filter sample position and a filter exchange position, a particulate filter of said multiple particulate filters being sealed within said filter holder/exchange mechanism when in said filter sample position, and when in said filter exchange position said holder/exchange mechanism being open with said particulate filter vertically and horizontally displaced from said filter sample position to facilitate manual removal/replacement of said particulate filter; and vacuum pump means for establishing air flow into a selected airborne particulate intake of said multiple airborne particulate intakes, said air flow containing airborne particulate for sampling by said particulate filter.

33. The manual sampling monitor of claim 32, wherein a designated particulate filter of said multiple particulate filters and its airborne particulate intake comprise a satellite unit, and said satellite unit is remote from said vacuum pump means.

34. A manual sampling monitor for collecting airborne particulate, said manual sampling monitor comprising:

multiple airborne particulate intakes for accepting air flow containing airborne particulate;

multiple particulate filters of which each particulate filter is coupled to its own airborne particulate intake of said multiple airborne particulate intakes for sampling accepted airborne particulate;

vacuum pump means for establishing air flow into a selected airborne particulate intake of said multiple airborne particulate intakes, said air flow containing airborne particulate for sampling by a particulate filter of said multiple particulate filters that corresponds to said selected airborne particulate intake; and automated sampling control means coupled to said vacuum pump means for control of said vacuum pump means' establishing of air flow into said selected airborne particulate intake, said sampling control means having means for receiving external condition dependent data and for employing at least some of said external condition dependent data for conditional activation of said vacuum pump means' establishing of air flow into said selected airborne particulate intake.

35. The manual sampling monitor of claim 34, wherein a selected particulate filter of said multiple particulate filters and its airborne particulate intake comprise a satellite unit, and said satellite unit having said selected particulate filter is remote from said automated sampling control means.

36. A monitor for manual sampling of airborne particulate, said monitor comprising:

multiple airborne particulate intakes for accepting air flow containing airborne particulate;

multiple particulate filters of which each particulate filter is coupled to its own airborne particulate intake of said multiple airborne particulate intakes for sampling accepted airborne particulate;

means for establishing air flow containing airborne particulate into a selected airborne particulate intake of said multiple airborne particulate intakes; and means for raising the temperature of air flow within said monitor, wherein once a selected particulate filter of said multiple particulate filters is manually removed from said manual sampling monitor, particulate collected by said selected particulate filter can be immediately analyzed.

37. The manual sampling monitor of claim 36, wherein a designated particulate filter of said multiple particulate filters and its airborne particulate intake comprise a satellite unit, and said satellite unit having said designated particulate filter is remote from any other filter of said at least two filters of said particulate sampling apparatus.

* * * * *

UNITED STATES PATENT AND TRADEMARK OFFICE
CERTIFICATE OF CORRECTION

PATENT NO. : 5,553,507
DATED      : September 10, 1996
INVENTOR(S) : Basch, et al It is certified that error appears in the above-indentified patent and that said Letters Patent is hereby corrected as shown below:

<u>In the title:</u>

In item [54] "AIRBORNE PARTICULATE" should read --AIRBORNE PARTICULATE SAMPLING MONITOR--

In column 1, line 1 "AIRBORNE PARTICULATE" should read --AIRBORNE PARTICULATE SAMPLING MONITOR--

<u>In the claims:</u>

In column 12, line 8, "monitors" should read --monitor--.

Signed and Sealed this

Seventh Day of January, 1997

Attest:

BRUCE LEHMAN

*Attesting Officer*          *Commissioner of Patents and Trademarks*